(12) United States Patent
Federspiel et al.

(10) Patent No.: US 12,114,851 B2
(45) Date of Patent: Oct. 15, 2024

(54) REDUCED FRICTION KNOTLESS SUTURE ROUTING

(71) Applicant: Acumed LLC, Hillsboro, OR (US)

(72) Inventors: Joshua P. Federspiel, Portland, OR (US); Matt Sucec, Portland, OR (US); Andrew Seykora, Portland, OR (US); Mark Sommers, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 801 days.

(21) Appl. No.: 17/244,538

(22) Filed: Apr. 29, 2021

(65) Prior Publication Data

US 2021/0338231 A1    Nov. 4, 2021

Related U.S. Application Data

(60) Provisional application No. 63/018,187, filed on Apr. 30, 2020.

(51) Int. Cl.
*A61B 17/04*    (2006.01)

(52) U.S. Cl.
CPC ...... *A61B 17/0466* (2013.01); *A61B 17/0401* (2013.01); *A61B 2017/0404* (2013.01)

(58) Field of Classification Search
CPC ............ A61B 17/0466; A61B 17/0401; A61B 2017/0404; A61B 2017/0414; A61B 2017/0417; A61B 2017/0477; A61B 2017/0459; A61B 2017/0419; A61F 2/0811

See application file for complete search history.

(56) References Cited

U.S. PATENT DOCUMENTS

| | | | |
|---|---|---|---|
| 11,109,855 B2 | 9/2021 | Shoshtaev et al. | |
| 2006/0293709 A1 | 12/2006 | Bojarski et al. | |
| 2011/0022061 A1 | 1/2011 | Orphanos et al. | |
| 2018/0249998 A1* | 9/2018 | Chavan | A61B 17/0401 |
| 2020/0093514 A1 | 3/2020 | Perez et al. | |

OTHER PUBLICATIONS

International Search Report corresponding to related International Patent Application No. PCT/US2021/029949 mailed Aug. 5, 2021, 3 pages.

(Continued)

*Primary Examiner* — Dianne Dornbusch
(74) *Attorney, Agent, or Firm* — K&L Gates LLP

(57) ABSTRACT

A new and innovative method of routing a strand of material for creating a self-locking construct that joins two objects is provided. More specifically, the provided routing method includes a crossover point at which the routed strand of material crosses over itself thereby enabling the strand portions routed through one of the objects to travel in a same direction when the self-locking construct is cinched. The strand portions traveling in the same direction generates less friction between the portions than if the portions traveled in opposite directions. Accordingly, the provided routing method helps enable a self-locking construct that generates less friction than typical self-locking constructs, which thereby helps reduce the occurrences of weaknesses in the final self-locking construct. The reduced friction generation also helps increase an ease of use for a user when cinching the self-locking construct.

13 Claims, 7 Drawing Sheets

(56) References Cited

OTHER PUBLICATIONS

International Written Opinion corresponding to related International Patent Application No. PCT/US2021/029949 mailed Aug. 5, 2021, 5 pages.
Supplementary Partial European Search Report from European Patent Application No. 21797673.7, mailed Mar. 11, 2024. 6 pages.
International Preliminary Report corresponding to related International Patent Application No. PCT/US2021/029949 mailed Nov. 10, 2022, 7 pages.

* cited by examiner

REDUCED FRICTION KNOTLESS SUTURE ROUTING

PRIORITY CLAIM

The present application claims priority to and the benefit of U.S. Provisional Application 63/018,187, filed Apr. 30, 2020, the entirety of which is herein incorporated by reference.

BACKGROUND

Suture may be woven, or routed, through itself between two objects such that the suture is self-locking. Typical methods for routing suture to create this self-locking construct, however, can result in friction being generated at the suture's loose end that causes the formation suture loops. These suture loops can get trapped between one of the objects and the surface that the object is cinched down to, which may cause user frustration and/or a weakness in the final self-locking suture construct. Accordingly, a need exists for suture routing that reduces or eliminates suture loop formation when cinching two objects together.

SUMMARY

The present disclosure provides a new and innovative method of routing a strand of material (e.g., suture) for creating a self-locking suture construct that joins two objects. Compared to suture routed by typical methods, the provided routing method results in reduced friction between portions of the suture, and thereby reduced suture loop formation, as the routed suture is cinched between two objects. The reduction in suture loop formation can increase the self-locking suture construct's ease-of-use for a user by helping prevent the suture from getting trapped between one of the objects and the surface that the object is cinched down to.

In an example, a method of routing a strand of material between a first object and a second object to thereby form a self-locking construct includes routing a leading end of the strand of material between the first object and the second object such that two portions of the strand of material are inserted through an opening in the first object and three portions of the strand of material are inserted through an opening in the second object, and such that when the leading end and a trailing end of the strand of material are tensioned each of the two portions of the strand of material inserted through the opening in the first object travel in a same direction.

In another example, a self-locking construct includes a first object including a first opening, a second object including a second opening, and a strand of material. A leading end of the strand of material is routed between the first object and the second object such that two portions of the strand of material are inserted through the first opening in the first object and three portions of the strand of material are inserted through the second opening in the second object, and such that when the leading end and a trailing end of the strand of material are tensioned each of the two portions of the strand of material inserted through the first opening in the first object travel in a same direction.

In another example, a method of routing a strand of material between a first object and a second object to thereby form a self-locking construct includes inserting a leading end of the strand of material through a second opening of the second object such that the leading end enters on a second side of the second opening and exits on a first side of the second opening. The leading end of the strand of material is then inserted through a first opening of the first object such that the leading and enters on a first side of the first opening and exits on a second side of the first opening. The leading end of the strand of material is then inserted through the second opening of the second object such that the leading end enters on the first side of the second opening and exits on the second side of the second opening, thereby crossing the leading end of the strand of material over a portion of the strand of material. The leading end of the strand of material is then inserted through the first opening of the first object such that the leading end enters on the second side of the first opening and exits on the first side of the first opening. The leading end of the strand of material is then inserted through the second opening of the second object such that the leading end enters on the second side of the second opening and exits on the first side of the second opening.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

Figure 5:
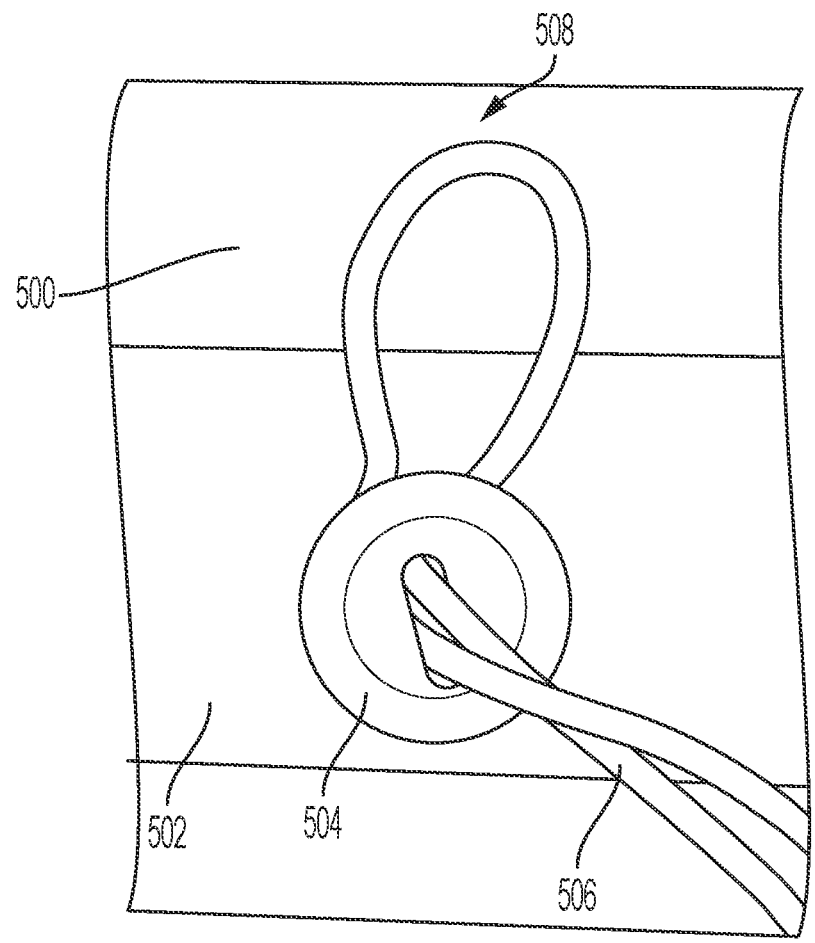
FIG. 5 illustrates a perspective view of an example suture loop formed as the result of typical suture routing methods for creating a self-locking construct.

The present disclosure provides a new and innovative method of routing a strand of material (e.g., suture) for creating a self-locking suture construct that joins two objects. More specifically, the provided suture routing method includes a crossover point at which the routed suture crosses over itself thereby enabling the suture portions routed through one of the objects to travel in a same direction when the suture is cinched. The suture portions traveling in the same direction generates less friction between the portions than if the portions traveled in opposite directions. The generation of less friction helps prevent the formation of suture loops that may be cinched between an object and the surface it is cinched to, which may happen for typical suture routing methods for creating a self-locking construct. For example, FIG. 5 illustrates a loop 508 of suture 506 that is cinched between an object 504 and the surface of the plate 502 that the object is cinched to. The plate 502 is against a bone 500. The loop 508 was formed as the result of typical suture routing methods for creating a self-locking construct in this example.

An object joined by the provided self-locking suture construct may be any suitable object for cinching together with a separate object. In some examples, an object joined by the self-locking suture construct may be a surgical button. In other examples, an object joined by the self-locking suture construct may be a surgical anchor. For instance, a surgical button may be joined to another surgical button, or to a surgical anchor, by the self-locking suture construct.

While the present description describes the provided routing method in relation to suture, it will be appreciated that the provided routing method may be performed with any suitable strand of material (e.g., rope, string, etc.) to cinch two objects together.

Figure 1A:
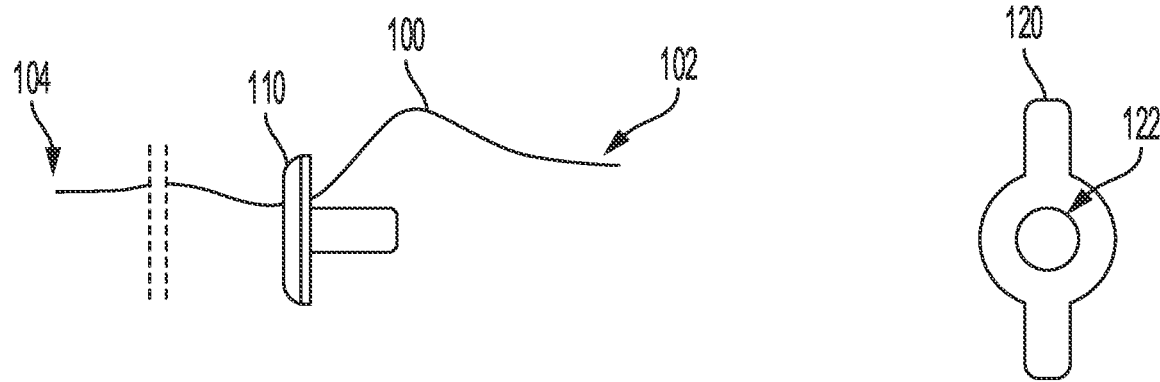
FIGS. 1A to 1H illustrate portions of an example method of routing a strand of material between two objects to form a self-locking construct, according to an aspect of the present disclosure.
Figure 1B:
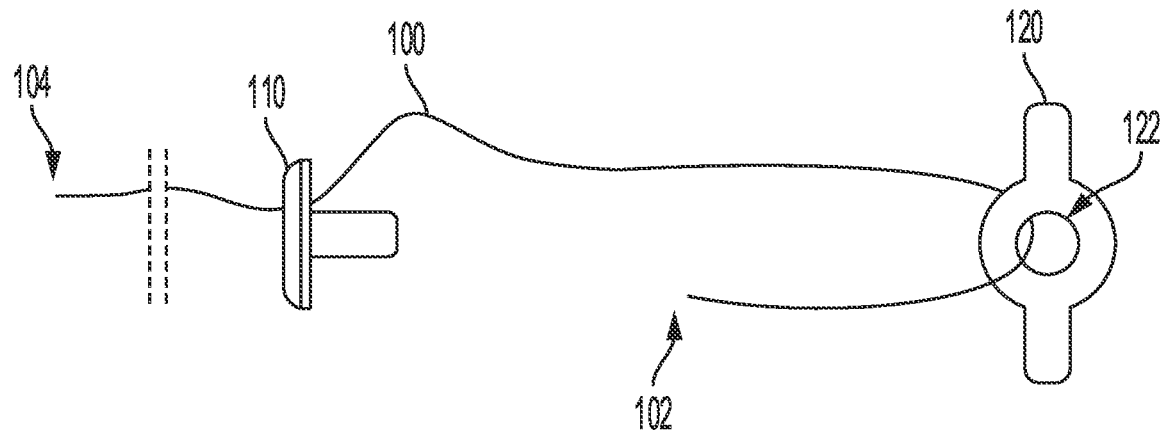
Figure 1C:
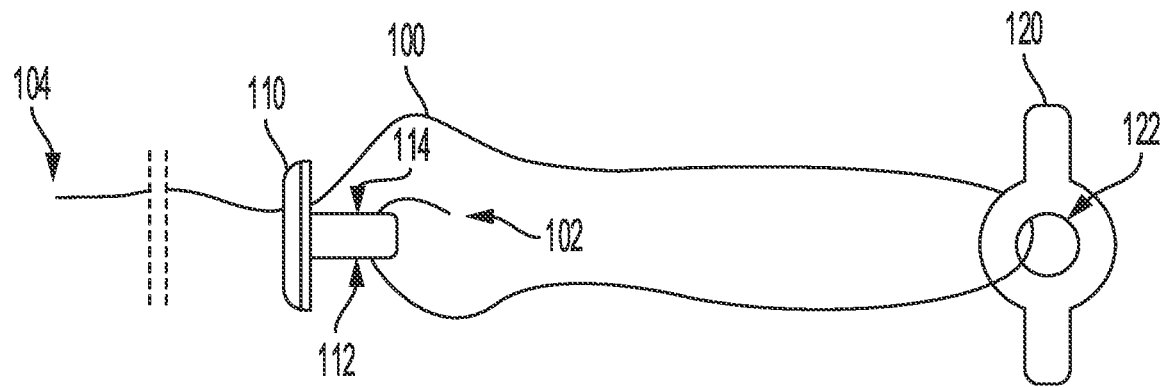
Figure 3:
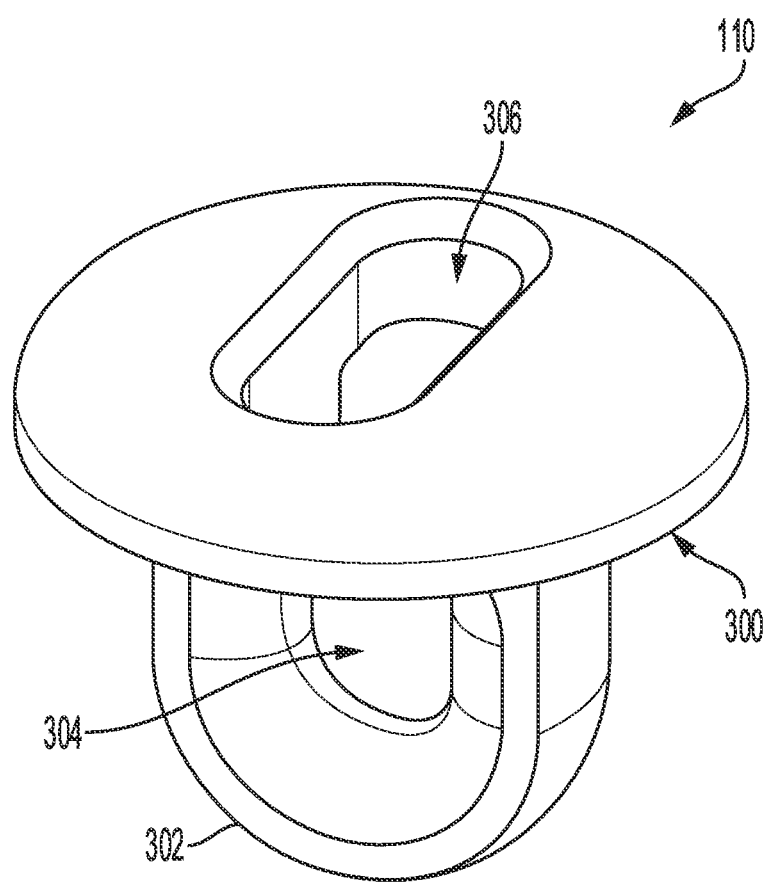
FIG. 3 illustrates a perspective view of an example first object of FIGS. 1A to 1H, according to an aspect of the present disclosure.
Figure 4:
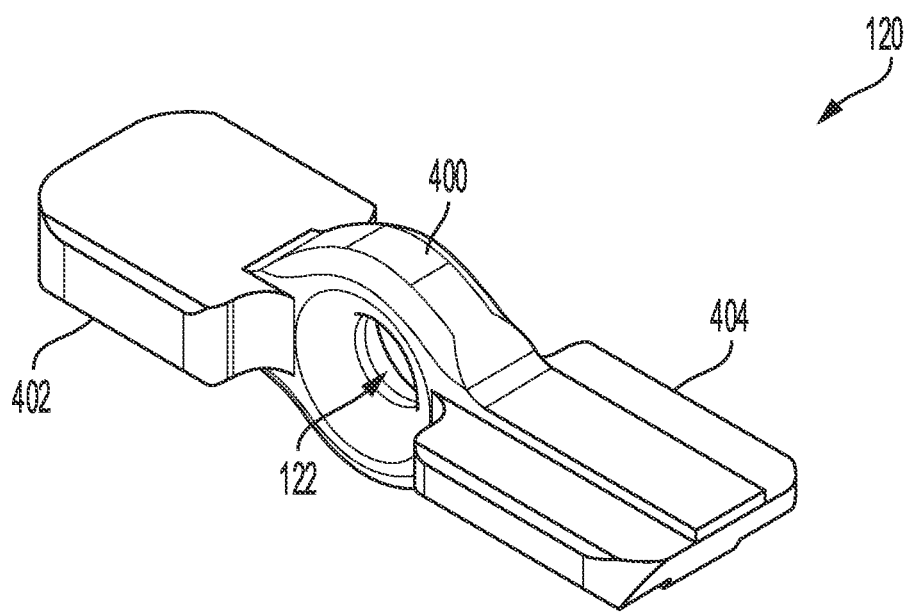
FIG. 4 illustrates a perspective view of an example second object of FIGS. 1A to 1H, according to an aspect of the present disclosure.

FIGS. 1A to 1H illustrate portions of an example method of routing a strand of material 100 (e.g., suture) between a first object 110 (e.g., a surgical button) and a second object 120 (e.g., a surgical button) to thereby form a self-locking construct 130. It should be appreciated that the illustrated form/shape of the first object 110 and the second object 120 is merely exemplary and in other examples the first object 110 and/or the second object 120 may have other suitable forms/shapes. Perspective views of the example first object 110 and the example second object 120 are shown in FIGS. 3 and 4 respectively. Returning to FIGS. 1A to 1H, the strand of material 100 includes a leading end 102 and a trailing end 104. The first object 110 includes an opening 304 (FIG. 3). A first side 112 and a second side 114 of the opening 304 are indicated in FIG. 1C, though not in the other figures solely for illustrative clarity. In some aspects, the first object 110 may include an opening 306 (FIG. 3). The second object 120 includes an opening 122. A first side of the opening 122 is visible in FIGS. 1A to 1H, while a second side of the opening 122 is opposite the first side and not visible in FIGS. 1A to 1H.

In some aspects, the example routing method may begin by inserting the leading end 102 of the strand of material 100 through the opening 306 of the first object 110, as shown in FIG. 1A. The leading end 102 of the strand of material 100 may then be inserted through the opening 122 of the second object 120 such that the leading end 102 enters the opening 122 at its second side and exits the opening 122 at its first side, as shown in FIG. 1B. In some aspects, the first object 110 might not include the opening 306, and in such aspects, the example routing method may begin with inserting the leading end 102 of the strand of material 100 through the opening 122 of the second object 120 such that the leading end 102 enters the opening 122 at its second side and exits the opening 122 at its first side. For example, the first object 110 may be replaced by a second object 120 and the strand of material 100 may be routed between two separate second objects 120 that each only include the opening 122.

Figure 1D:
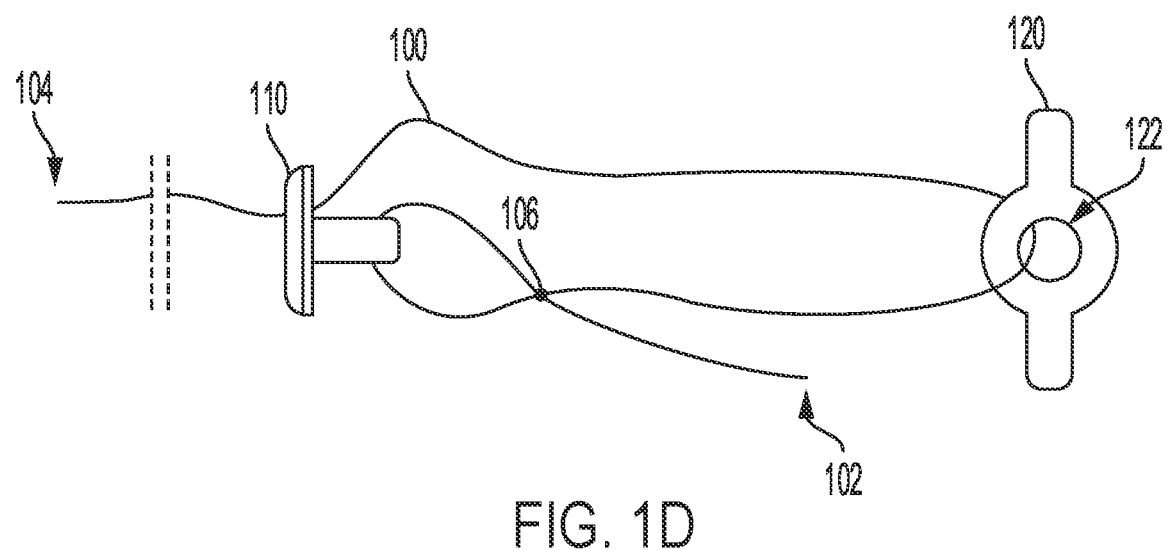
Figure 1E:
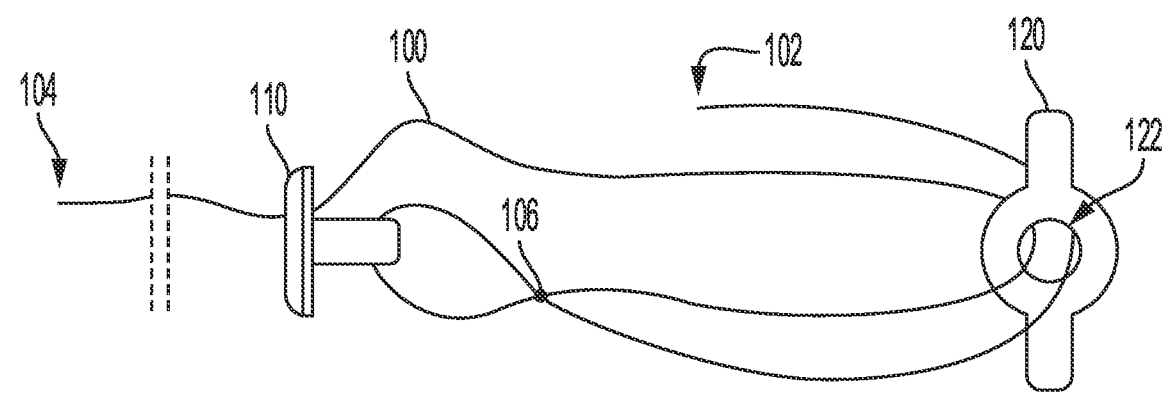

The leading end 102 of the strand of material 100 may then be inserted through the opening 304 of the first object 110 such that the leading end 102 enters the opening 304 at its first side 112 and exits the opening 304 at its second side 114, as shown in FIG. 1C. The leading end 102 of the strand of material 100 may then be routed such that the strand of material 100 crosses over itself (e.g., at the crossover point 106), as shown in FIG. 1D. The leading end 102 of the strand of material 100 is thereafter routed through the opening 122 of the second object 120 such that the leading end 102 enters the opening 122 at its first side and exits the opening 122 at its second side, as shown in FIG. 1E. Stated differently, the leading end 102 is inserted into the same side (e.g., the first side) of the opening 122 of the second object 120 as the side from which the leading end 102 last exited the opening 122 (e.g., compare FIGS. 1B and 1E). Though not illustrated for the sake of clarity, the leading end 102 of the strand of material 100 may be routed through one or more openings formed in the strand of material 100 as the leading end 102 is routed through the opening 122. Stated differently, as will be appreciated by one having skill in the art, the strand of material 100 is routed through itself as the leading end 102 is routed through the opening 122 as part of the formation of the self-locking nature of the self-locking construct 130.

Figure 1F:
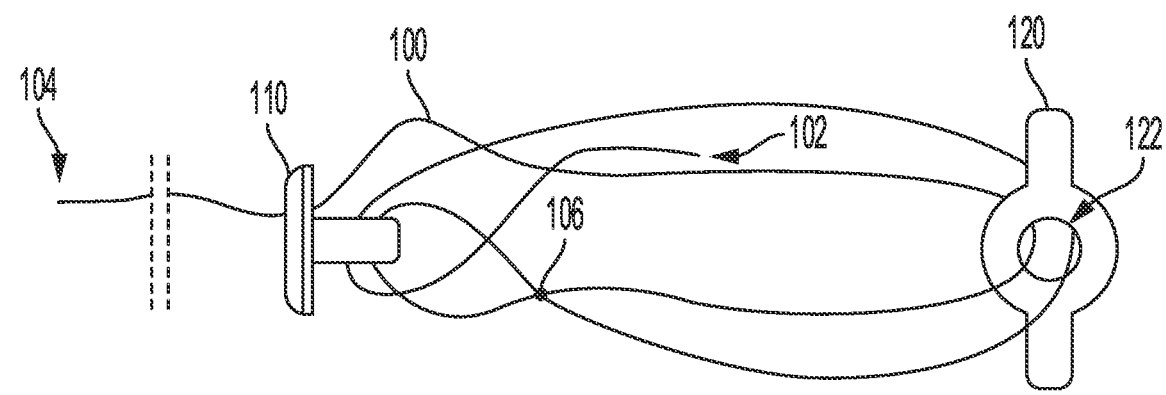
Figure 1G:
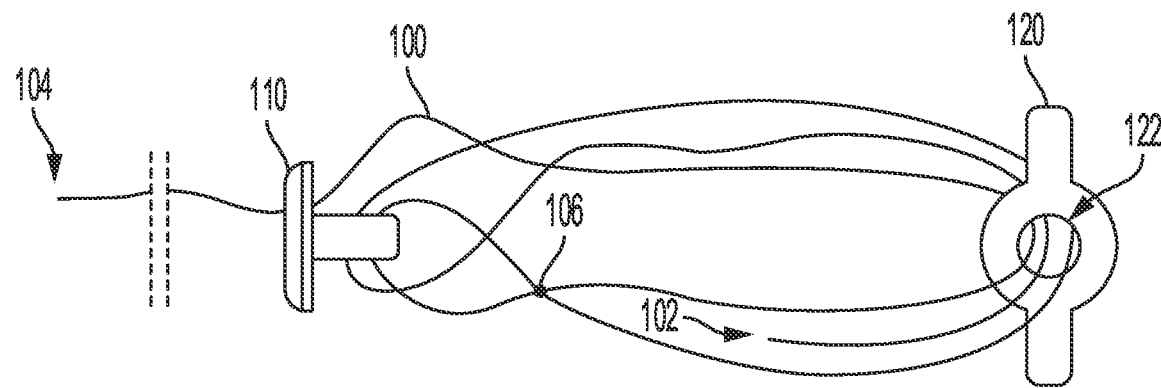
Figure 1H:
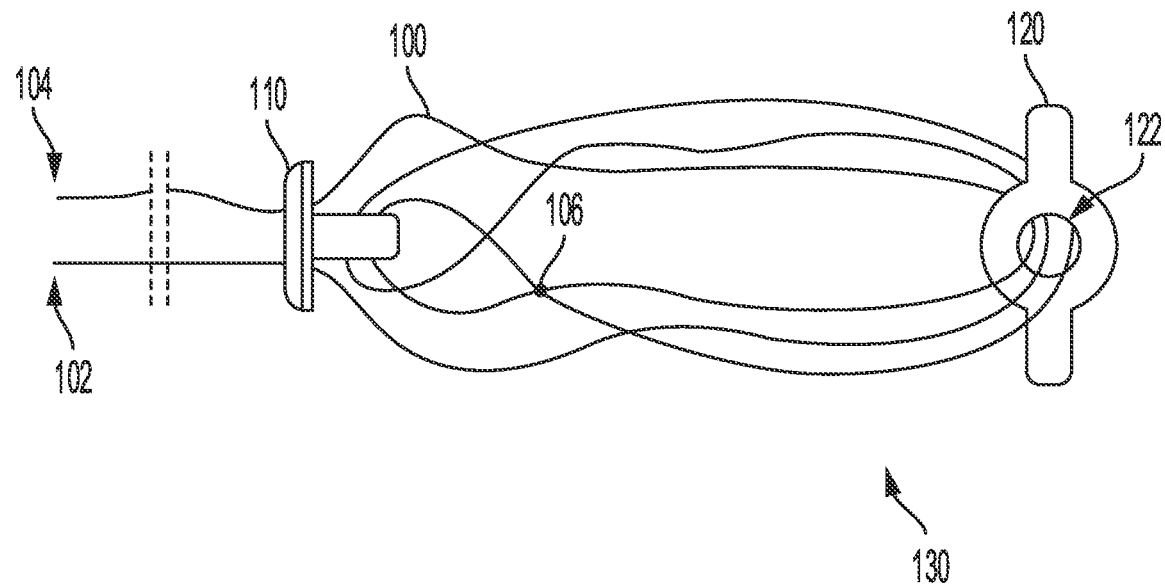

The leading end 102 of the strand of material 100 may then be inserted through the opening 304 of the first object 110 such that the leading end 102 enters the opening 304 at its second side 114 and exits the opening 304 at its first side 112, as shown in FIG. 1F. The leading end 102 of the strand of material 100 is then routed through the opening 122 of the second object 120 such that the leading end 102 enters the opening 122 at its second side and exits the opening 122 at its first side, as shown in FIG. 1G. Stated differently, the leading end 102 is inserted into the same side (e.g., the second side) of the opening 122 of the second object 120 as the side from which the leading end 102 last exited the opening 122 (e.g., compare FIGS. 1E and 1G). As with FIG. 1E, though not illustrated, the leading end 102 of the strand of material 100 may again be routed through one or more openings formed in the strand of material 100 as the leading end 102 is routed through the opening 122. Stated differently, as will be appreciated by one having skill in the art, the strand of material 100 is routed through itself as the leading end 102 is routed through the opening 122 as part of the formation of the self-locking nature of the self-locking construct 130.

In some aspects, the leading end 102 of the strand of material 100 may then be inserted through the opening 306 of the object 110 such that the leading end 102 meets the trailing end 104 of the strand of material 100. In other aspects, the leading end 102 of the strand of material may be brought past the first object 110 relative to the second object 120 to meet the trailing end 104 of the strand of material. For instance, the first object 110 might not include an opening 306 in such aspects. Once the leading end 102 and the trailing end 104 of the strand of material 100 are on the same side of the first object 110 the example routing method may be complete, thereby forming a self-locking construct 130. In some aspects, the leading end 102 and the trailing end 104 may be joined at a connection point 200 (e.g., FIG. 2), such as by a knot.

It should be appreciated that the preceding example routing method may alternatively be performed in reverse. For instance, the leading end 102 and the trailing end 104 of the strand of material 100 may be switched and the leading end 102 may be routed between the first object 110 and the second object 120 such that the leading end 102 follows the illustrated routing in reverse order (e.g., from FIG. 1H to FIG. 1A).

Figure 2:
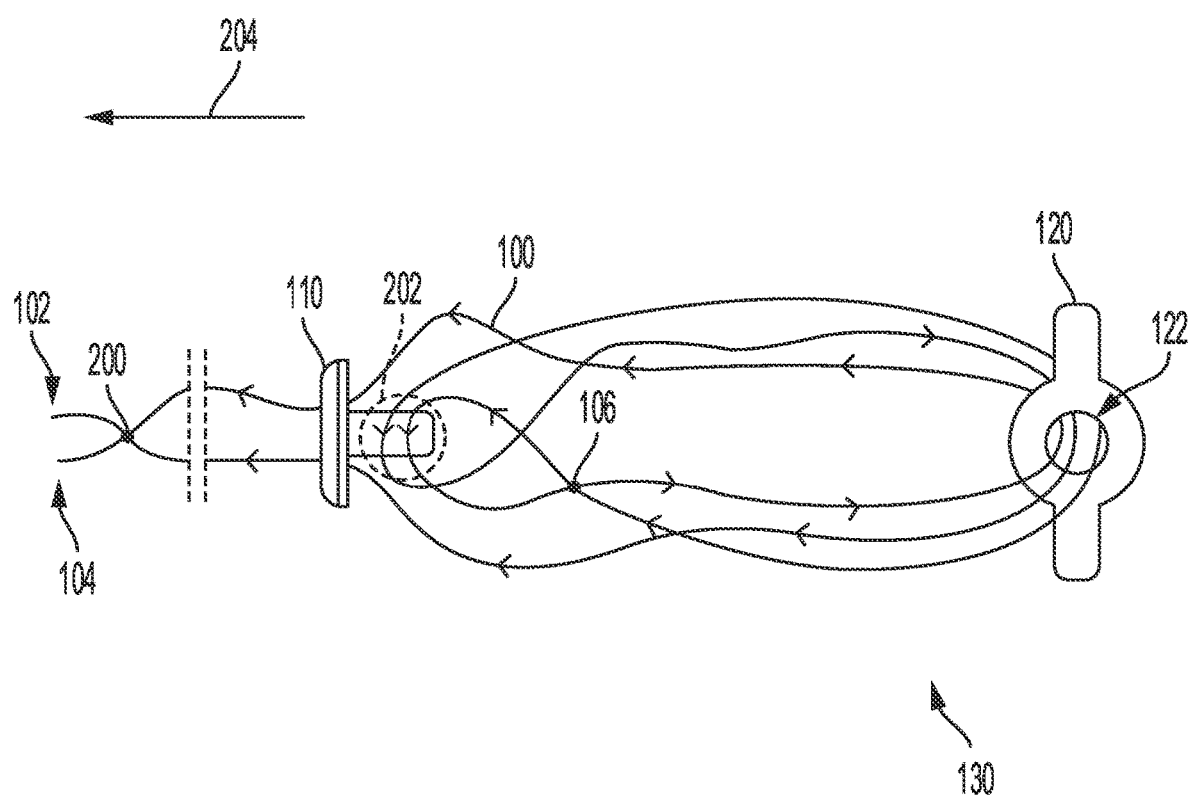
FIG. 2 illustrates a schematic of the movement of various portions of the strand of material of FIGS. 1A to 1H as the leading and trailing ends of the strand of material are pulled, according to an aspect of the present disclosure.

With the self-locking construct 130 assembled and the first and second objects 110 and 120 held in position (e.g., by a bone), the leading end 102 and the trailing end 104 of the strand of material 100 may be tensioned, or pulled, to introduce tension in the strand of material 100 and cinch the first object 110 and the second object 120 together FIG. 2 illustrates a schematic of the movement of various portions of the strand of material 100, shown by the illustrated arrowheads, as the leading end 102 and the trailing end 104 of the strand of material 100 are pulled in the direction of the arrow 204. While nothing is shown against the first object 110 nor the second object 120 in FIG. 2, it can be assumed that the first object 110 and the second object 120 are maintained in their respective positions as the leading end 102 and the trailing end 104 of the strand of material 100 are pulled.

The first object 110 is illustrated as transparent in FIG. 2 in order to see the portions of the strand of material 100 routed through the opening 304 and the opening 306. Highlighted by the dashed circle 202, it can be seen that each of the two portions of the strand of material 100 routed through the opening 304 of the first object 110 travel in the same direction as the leading end 102 and the trailing end 104 of the strand of material 100 are pulled. As will be appreciated in view of the preceding description of the example routing method, this same direction of travel for both portions of the strand of material 100 routed through the opening 304 is enabled by including the crossover point 106 in the routing method.

The same direction of travel for both portions of the strand of material 100 routed through the opening 304 helps reduce friction between these portions of the strand of material 100. For instance, if these two portions traveled in opposite directions they would rub against one another to a greater degree than the two portions traveling in the same direction. As such, more friction would be created by the two portions traveling in opposite directions. In some instances, the created friction could interfere with, or affect, the travel of portions of the strand of material 100 as the leading end 102 and the trailing end 104 of the strand of material 100 are pulled, thereby causing the formation of loops of the strand of material 100. These loops can get trapped between the first object 110 and the surface it is cinched to, which can create a weakness in the final self-locking construct 130 and/or reduce ease of use for a user when cinching the self-locking construct 130. Accordingly, the provided method of routing a strand of material 100 helps enable a self-locking construct 130 that generates less friction than typical self-locking constructs, which thereby helps increase an ease of use for a user when cinching the self-locking construct 130 by reducing the formation of loops. In some instances, the reduction of loop formation helps reduce the occurrences of weaknesses in the final self-locking construct.

FIG. 3 illustrates a perspective view of an example first object 110. In this example, the first object 110 is a surgical button that may be installed in a patient. The example first object 110 may include a head 300 integral with or attached to a peg 302. The opening 304 of the example first object 110 is defined by the peg 302. The head 300 includes the opening 306 of the example first object 110.

FIG. 4 illustrates a perspective view of an example second object 120. In this example, the second object 120 is a surgical button that may be installed in the patient. The example second object 120 may include a base 400 integral to or connected with a wing 402 and a wing 404 that extends from the base 400. The opening 122 of the example second object 120 is defined by the base 400.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A method of routing a strand of material between a first object and a second object to thereby form a self-locking construct, the method comprising:

routing a leading end of the strand of material between the first object and the second object such that two portions of the strand of material are inserted through an opening in the first object and three portions of the strand of material are inserted through an opening in the second object, and such that when the leading end and a trailing end of the strand of material are tensioned each of the two portions of the strand of material inserted through the opening in the first object travel in a same direction, wherein routing the leading end of the strand of material includes:

inserting the leading end of the strand of material through the opening of the second object such that the leading end enters on a second side of the opening of the second object and exits on a first side of the opening of the second object;

subsequently inserting the leading end of the strand of material through the opening of the first object such that the leading and enters on a first side of the opening of the first object and exits on a second side of the opening of the first object; and subsequently inserting the leading end of the strand of material through the opening of the second object such that the leading end enters on the first side of the opening in the second object and exits on the second side of the opening in the second object, thereby crossing the leading end of the strand of material over a portion of the strand of material.

2. The method of routing a strand of material of claim 1, wherein the strand of material is suture.

3. The method of routing a strand of material of claim 1, wherein the strand of material is rope or string.

4. The method of routing a strand of material of claim 1, wherein the first object is a surgical button or surgical anchor.

5. The method of routing a strand of material of claim 1, wherein the second object is a surgical button or surgical anchor.

6. The method of routing a strand of material of claim 1, wherein the first object is a surgical button or surgical anchor and the second object is a surgical button or surgical anchor.

7. The method of routing a strand of material of claim 1, wherein the opening in the first object is a first opening in the first object, the first object further including a second opening, and wherein the leading end and the trailing end of the strand of material are positioned through the second opening of the first object.

8. A method of routing a strand of material between a first object and a second object to thereby form a self-locking construct, the method comprising:

inserting a leading end of the strand of material through a second opening of the second object such that the leading end enters on a second side of the second opening and exits on a first side of the second opening;

subsequently inserting the leading end of the strand of material through a first opening of the first object such that the leading and enters on a first side of the first opening and exits on a second side of the first opening;

subsequently inserting the leading end of the strand of material through the second opening of the second object such that the leading end enters on the first side of the second opening and exits on the second side of the second opening, thereby crossing the leading end of the strand of material over a portion of the strand of material;

subsequently inserting the leading end of the strand of material through the first opening of the first object such that the leading end enters on the second side of the first opening and exits on the first side of the first opening; and subsequently inserting the leading end of the strand of material through the second opening of the second object such that the leading end enters on the second side of the second opening and exits on the first side of the second opening.

9. The method of routing a strand of material of claim 8, wherein subsequent to inserting the leading end of the strand of material through the second opening of the second object such that the leading end enters on the second side of the second opening and exits on the first side of the second opening, the method further comprises inserting the leading end of the strand of material through a third opening of the first object.

10. The method of routing a strand of material of claim 9, wherein a trailing end of the strand of material is positioned through the third opening.

11. The method of routing a strand of material of claim 8, wherein the first object is a surgical button or surgical anchor.

12. The method of routing a strand of material of claim 8, wherein the second object is a surgical button or surgical anchor.

13. The method of routing a strand of material of claim 8, wherein the first object is a surgical button or surgical anchor and the second object is a surgical button or surgical anchor.

* * * * *